United States Patent
Monagle

[11] Patent Number: 5,892,364
[45] Date of Patent: Apr. 6, 1999

[54] TRACE CONSTITUENT DETECTION IN INERT GASES

[76] Inventor: Matthew Monagle, 9220 Jill Patricia, NW., Albuquerque, N. Mex. 87114

[21] Appl. No.: 927,738

[22] Filed: Sep. 11, 1997

[51] Int. Cl.[6] ................................................. G01N 27/62
[52] U.S. Cl. ..................... 324/464; 324/459; 73/28.02; 436/35
[58] Field of Search .................... 324/459, 464, 324/465, 466, 467, 468, 469, 470, 71.1; 250/251, 281; 73/23.35, 23.4, 23.42, 28.01, 28.02; 313/231.41; 315/111.91; 436/35, 38, 153

[56] References Cited

U.S. PATENT DOCUMENTS

| | | | |
|---|---|---|---|
| 3,545,863 | 12/1970 | Mansell et al. | 356/86 |
| 4,148,612 | 4/1979 | Taylor et al. | 436/35 |
| 4,150,951 | 4/1979 | Capelle et al. | 436/35 |
| 4,225,235 | 9/1980 | Anderson et al. | 356/316 |
| 4,255,052 | 3/1981 | Anderson | 356/316 |
| 4,309,187 | 1/1982 | Dodge, III et al. | 436/35 |
| 4,427,633 | 1/1984 | Peacock et al. | 422/83 |
| 4,586,368 | 5/1986 | Rice et al. | 73/23.4 |
| 4,705,948 | 11/1987 | Ramsey et al. | 250/386 |
| 4,740,695 | 4/1988 | Simpson | 250/282 |
| 4,789,783 | 12/1988 | Cook | 250/379 |
| 4,801,209 | 1/1989 | Wadlow | 356/416 |
| 4,851,683 | 7/1989 | Yang et al. | 250/339.03 |
| 4,873,862 | 10/1989 | Scott et al. | 73/23.4 |
| 5,062,707 | 11/1991 | Adler-Golden et al. | 356/311 |
| 5,085,599 | 2/1992 | Maejima et al. | 439/595 |
| 5,153,519 | 10/1992 | Wentworth et al. | 324/464 |
| 5,192,865 | 3/1993 | Zhu | 250/288 |
| 5,317,271 | 5/1994 | Wentworth et al. | 324/464 |
| 5,394,091 | 2/1995 | Wentworth et al. | 324/464 |
| 5,404,219 | 4/1995 | D'Silva | 356/316 |
| 5,528,150 | 6/1996 | Stearns et al. | 324/464 |
| 5,594,346 | 1/1997 | Stearns | 324/464 |
| 5,665,604 | 9/1997 | Monagle et al. | 436/139 |

OTHER PUBLICATIONS

Eliasson, Baldur, *Modeling and Applications of Silent Discharge Plasmas, IEEE Transactions on Plasma Science,* vol. 19, pp. 309–323, Apr. 1991.

Olah, K., et al., *On the Mechanism of Kolb's N–P Selective Detector,* Dept of Physical Chemistry, Polytechnical University of Budapest, H–1521, pp. 497–502, Budafoki ut 8, Hungary, Sep. 1979.

Sutton, D. G., et al., *Chemiluminescence Detector Based on Active Nitrogen for Gas Chromatography of Hydrocarbons,* Analytical Chemistry, vol. 51, No. 9, pp. 1399–1401, Aug. 1979.

*Primary Examiner*—Diep N. Do
*Attorney, Agent, or Firm*—Jeffrey D. Myers

[57] ABSTRACT

A method and apparatus for the detection of trace constituents in inert gases. Three modes of operation of the said invention are most preferred. In the first embodiment, a dielectric barrier discharge cell receives an inert gas, excites the gas, and the gas is then allowed to mix with additional gas in which the constituent to be measured is entrained. Energy is then passed from the excited states of the inert gas to the analytes of interest creating charged analytes of interest which are then measured through the use of commercial electrometers. In a second embodiment, the dielectric barrier discharge device receives the analyte entrained within the inert gas and the gas and, in some cases, the analytes are excited. The excited species then pass on and any resulting ionized species are then detected through the use of an electrometer. In the third embodiment, the analyte is entrained within the inert gas in the presence of a second gaseous constituent, reacts with the gaseous constituent, and then passes on to a thermionic emitting source. The altered constituent is then selectively ionized by the thermionic source and this ion is measured by an electrometer.

13 Claims, 4 Drawing Sheets

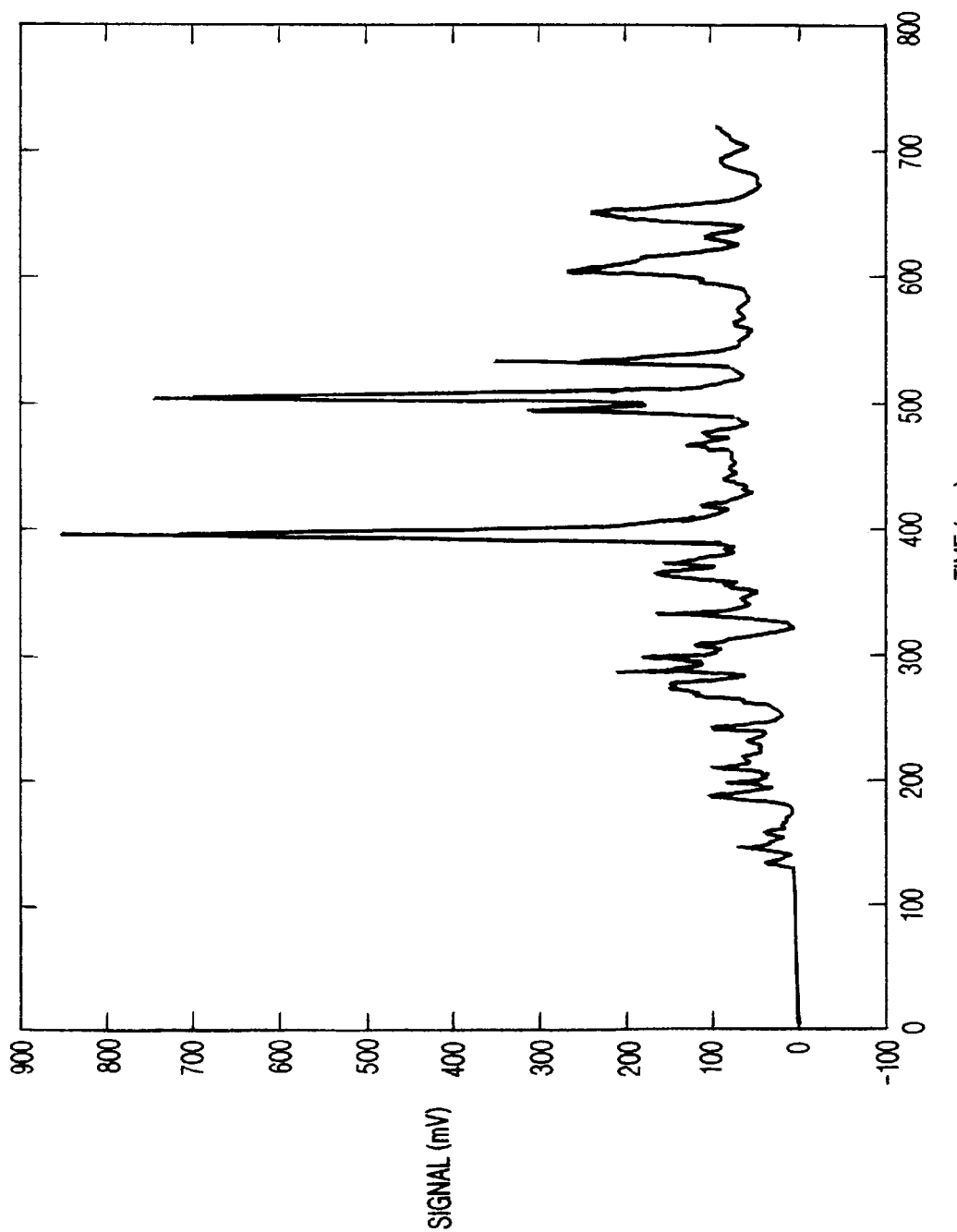

TRACE CONSTITUENT DETECTION IN INERT GASES

BACKGROUND OF THE INVENTION

1. Field of the Invention (Technical Field)

The present invention relates to methods of analyzing trace constituents present in inert gases and, more particularly, the measurement of trace analytes through the use of a dielectric barrier discharge. Still more particularly, it relates to the analysis of trace constituents which have become excited by their collision with an excited inert gas, the inert gas having been elevated to an excited state by its passage through a dielectric barrier discharge. The dielectric barrier discharge is formed from the application of high voltage alternating current to two electrodes placed in opposition separated by a dielectric material.

2. Background Art

The need to measure trace analytes is nearly the raison d'être for analytical chemistry. Whether the analytes are impurities which may affect an etching process in a semiconductor plant or they are trace levels of health-affecting pesticides in drinking water, the need to measure these analytes at low levels is very important. In view of these needs, new methods of determining trace level analytes are of growing importance.

Many different techniques have been identified for the measurement of trace analytes in inert gases. Capelle et al., U.S. Pat. No. 4,150,951, Taylor et al., U.S. Pat. No. 4,148,612, Ault, U.S. Pat. No. 3,545,863, and Dodge, III et al., U.S. Pat. No. 4,309,187, all disclose methods of spectroscopically measuring trace analytes in an inert gas through the use of various excitation sources. Dodge, III et al., details a process where a dielectric barrier discharge at low pressure is utilized to form metastable states of nitrogen which are then used to spectroscopically determine various metallic analytes such as zinc and mercury by their respective emission lines. Monagle et al., U.S. patent application Ser. No. 08/516,838, discloses a process wherein a dielectric barrier discharge plasma is used to oxidize halogenated hydrocarbons into their respective acid species which are subsequently measured. Scott et al., U.S. Pat. No. 4,873,862 and Simpson, U.S. Pat. No. 4,740,695, both disclose mechanisms for generating ionization within argon. Scott utilizes a thermal effect while Simpson discloses a means of ionizing argon using an ultraviolet source and a photoemissive element. These ionization processes are described as a means of creating metastable state species in argon in order to selectively ionize other constituents of interest. Stearns et al., U.S. Pat. Nos. 5,394,091 and 5,317,271, disclose a method of analyzing trace species in a gas stream using the ionization of the species through a charge transfer mechanism after it has come in contact with helium that has been put into an excited state. This excited state is obtained by a controlled, direct current (DC), pulsed spark discharge across two metal electrodes. The discharge is generated for a discrete time period as controlled by the circuitry identified in the patents identified. The balance of the time is spent with the discharge off, a state in which no additional excitation or ionization is taking place directly in the electrode path.

The methods identified above as well as the commercially available methods of doing the same have several drawbacks. To measure emission lines requires the support of a photomultiplier tube. Photomultiplier tubes yield the lowest noise at lower temperatures but chromatographic applications typically require the use of high temperatures to prevent analyte condensation. The methods identified by Simpson and Scott et al. will only yield limited quantities of ionized species which limits the linear range of detection. The use of exposed electrodes, as described by Wentworth et al. exposes the electrodes to contamination which will limit the useful operating life-time of the discharge system. Flame ionization based mechanisms, while they have been in use for many years, require several supporting gases and can, by their very nature, provide an ignition safety concern.

Accordingly, the need exists for a method of detecting trace constituents sensitively, with a large linear dynamic range, and with a simple and convenient apparatus. An additional capability to selectively identify materials is further desired.

SUMMARY OF THE INVENTION
(DISCLOSURE OF THE INVENTION)

The present invention is of a method for detection of trace constituents comprising: forming a dielectric barrier discharge by applying an alternating current voltage across a dielectric barrier material; elevating the inert gas to an excited state via the dielectric barrier discharge; mixing the excited state inert gas with trace analytes; and measuring with an electrometer matter selected from the group consisting of the analytes and their byproducts. In the preferred embodiment, elevating comprises maintaining the inert gas at a pressure above atmospheric pressure and at a temperature approximately at or above room temperature. Preferably, one or more reaction gases is passed through the dielectric barrier discharge, which gases may have one or more dopants.

The invention is further of a method of detecting analytes of interest comprising: commingling the analytes with an excited state reaction gas; passing the commingled analytes and reaction gas over a thermionic bead; and measuring with an electrometer matter selected from the group consisting of the analytes and their byproducts.

The invention is also of an analyte detection apparatus comprising: an inert gas source; a reaction cell; a dielectric barrier discharge cell connected to the inert gas source and the reaction cell wherein the dielectric barrier discharge cell excites the inert gas which is commingled with the analyte of interest to produce charged species; and an electrometer for measuring the species. In the preferred embodiment, the dielectric barrier discharge cell comprises a material selected from the group consisting of ceramic, quartz, and glass and an alternating current voltage source operating at a frequency between approximately 60 Hz and 100 kHz and at a voltage between approximately 1 kV and 100 kV. The inert gas source preferably comprises argon, helium, nitrogen, xenon, krypton, neon, or a mixture thereof. A bias voltage may be applied to the reaction chamber, a collector, or both, and may be applied continuously or be pulsed. The dielectric barrier discharge cell may comprise an electrode covered with a dielectric material.

Accordingly, it is an object of the invention to provide a method of analyzing trace amounts of analytes of interest including organic and inorganic materials through the transfer of energy from an excited state inert gas to the analyte of interest. The excited analyte of interest, or secondary products generated from the collision between the excited state gas and the analyte of interest, are then measured using an electrometer.

It is another object of the invention to provide a means of sensitively detecting trace level analytes when commuted in an inert carrier gas.

A further object of the invention is to provide a means of detecting analytes of interest without the use of sophisticated pulsing electronics and capable of operating in a variety of gases such as argon, nitrogen, and helium.

Another object of the invention is to provide selectivity in the detection of analytes in the inert gas through the use of different reaction gases such as argon or nitrogen and including reaction gases that contain dopants to reduce the ionization potential of the reactant gas.

Still another object of the invention is to provide selectivity in the detection of analytes in the inert gas through the use of dielectric packing materials to limit the ionization potential of the reactant gas.

It is a further object of the invention to provide a method of analyzing trace constituents through the use of a dielectric barrier discharge in conjunction with a thermionic source to selectively detect trace analytes present in an inert gas.

Yet another object of the invention is to provide such an analysis which has high sensitivity and a large linear range.

A further object of the invention is to provide a method which can be utilized with nitrogen as a carrier for the analytes of interest.

An additional object of the invention is to provide a method which is capable of being utilized at elevated temperatures and pressures.

Still another objective is to provide an improved apparatus for detecting trace analytes which is simpler and more convenient than known apparatus and is easier to operate.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings:

FIG. 5 is a representative output from the same embodiment of the apparatus using argon as the reactant gas.

DESCRIPTION OF THE PREFERRED EMBODIMENTS (BEST MODES FOR CARRYING OUT THE INVENTION)

The present invention is of a method and apparatus for the detection of trace constituents in inert gases. Three modes of operation of the said invention are most preferred. In the first embodiment, a dielectric barrier discharge cell receives an inert gas, excites the gas, and the gas is then allowed to mix with additional gas in which the constituent to be measured is entrained. Energy is then passed from the excited states of the inert gas to the analytes of interest creating charged analytes of interest which are then measured through the use of commercial electrometers. In a second embodiment, the dielectric barrier discharge device receives the analyte entrained within the inert gas and the gas and, in some cases, the analytes are excited. The excited species then pass on and any resulting ionized species are then detected through the use of an electrometer. In the third embodiment, the analyte is entrained within the inert gas in the presence of a second gaseous constituent, reacts with the gaseous constituent, and then passes on to a thermionic emitting source. The altered constituent is then selectively ionized by the thermionic source and this ion is measured by an electrometer.

Figure 1:
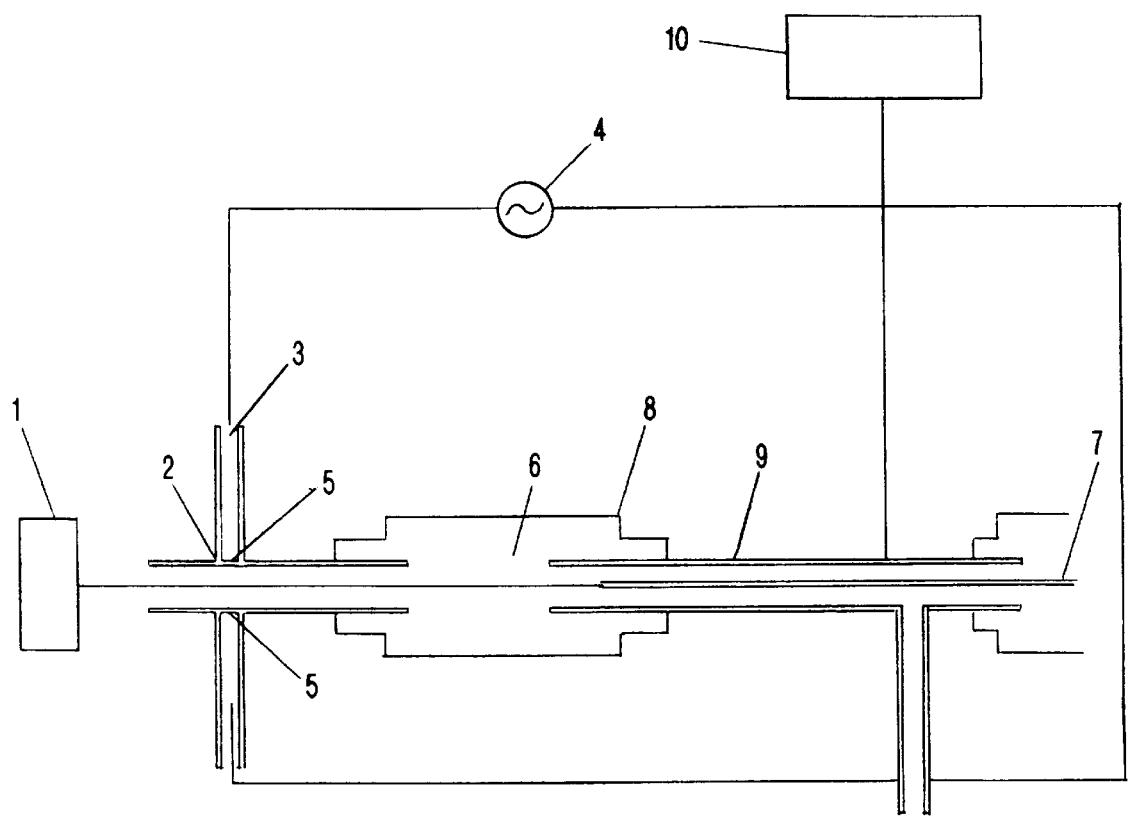
FIG. 1 is a schematic diagram of an embodiment of the apparatus of the invention.

The analytical detection of the invention is carried out by an apparatus such as that shown in FIG. 1. An inert gas such as nitrogen, helium, or argon, from a separate regulated source 1, is passed via a conduit into the discharge cell 2 where it is excited by the electrodes 3 which are connected to an appropriate high voltage, alternating current, power supply 4 across the dielectric barrier 5 comprising a material such as, but not limited to, ceramic, quartz, Pyrex, or glass. The excited gas is then conveyed to the reaction chamber 6 where it interacts with the species being measured. These species can be targeted analytes exuding from a gas chromatographic column 7 or entrained in a gas stream through other means (not shown). The excited species developed by electrodes 3 then react with the analyte species to create charged species. A voltage may be, if desired, applied to either to the reaction volume via a voltage source 8 or to the collector 9 via the electrometer 10. Ions or electrons formed are measured at the electrometer 10 which converts the signal to one that is recordable by current analytical instrumentation. The electrometer records changes in the current flowing through the cell as a result of the ionized species present in the reaction chamber and outputs a signal appropriate for a recording device (not shown). The combined effluent, column gas and reactant gas then proceed out the exhaust port 11. The electrometer and the dielectric barrier discharge (DBD) cell are preferably electrically isolated from the reaction region through the use of Teflon, polyimide, or ceramic insulators (not shown).

The species detected depends upon the bias applied to the collector or to the reaction chamber. For example, a positive voltage applied to the collector will measure negatively charged species, as will a negative voltage applied to the reaction chamber. An additional embodiment of the detector uses pulsed bias voltages in order to enhance the linearity of the detection mechanism as is performed in commercially available electron capture detectors which use radioactive sources.

Figure 2:
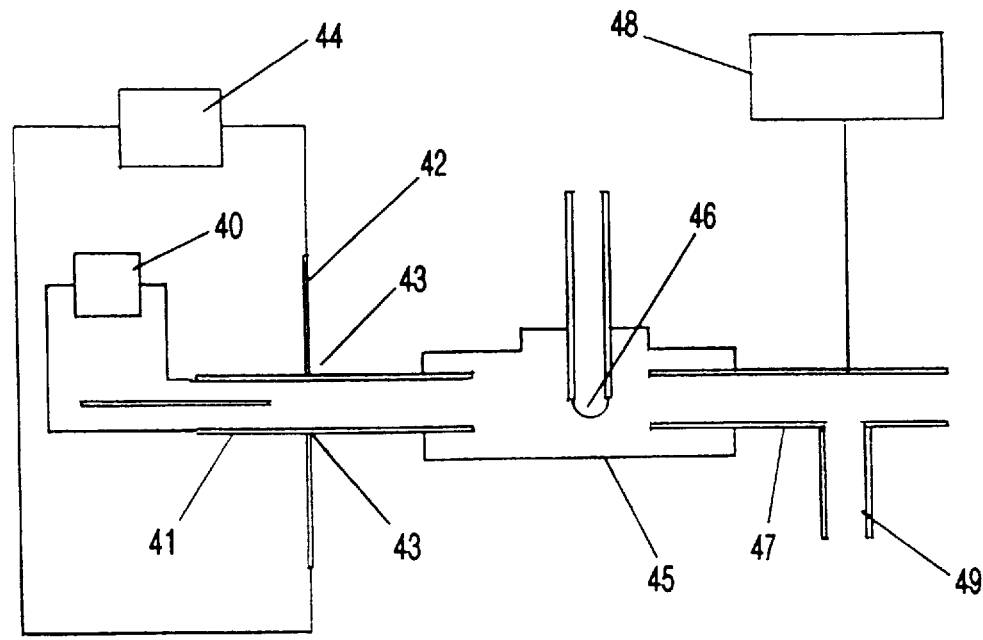
FIG. 2 is another embodiment of the apparatus of the invention utilizing a thermionic emitting source for additional ionization after the species have been subjected to the dielectric barrier discharge.

In another embodiment of the detector shown in FIG. 2, nitrogen from a separate regulated source 40 is conveyed to the discharge cell 41. The inert gas is excited by electrodes 42 which are separated from the cell by the dielectric barrier 43. Each of the electrodes is connected to an appropriate high voltage alternating current power supply 44. The application of high voltage generates the streamer process discussed below which in turn creates the excited species of inert gas. The excited species are then conveyed to the reaction chamber 45 where they are mixed with the analytes of interest. The excited species and the constituents of interest then undergo a decomposition process leading to the generation of intermediates which are amenable to measurement by thermionic emission sources. Upon mixing the excited reaction gas, both the analyte and the resultant carrier gases are allowed to flow by the thermionic emission source 46 maintained at an elevated temperature by a power supply (not shown) where additional excitement of the analytes of interest takes place. The excited species generated from contact with the thermionic emission source are then conveyed to a collector 47 which is connected to an electrometer 48. The electrometer then outputs the signal to an appropriate recording device (not shown). The combined effluent, column gas and reactant gas then proceed out the exhaust port 49. In varying the composition of the thermionic source and the reactant gases, the selectivity of the detector can be significantly enhanced.

Figure 3:
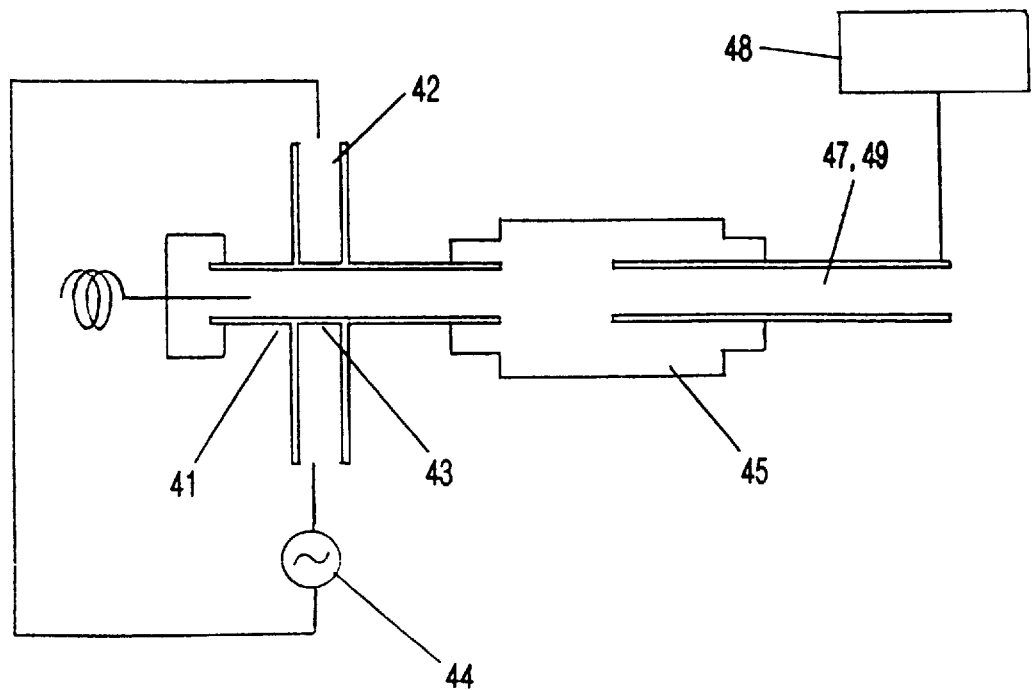
FIG. 3 is an additional embodiment of the apparatus of the invention in which both the analyte and the reaction gas are processed through the plasma contained within the dielectric barrier discharge (DBD) cell.

An additional embodiment of the detector, shown in FIG. 3, is one in which the effluent is directed directly through the silent discharge plasma and then conveyed through combined collector and exhaust port 47,49 and the residual ionized species are collected at the electrometer 48.

Figure 4:
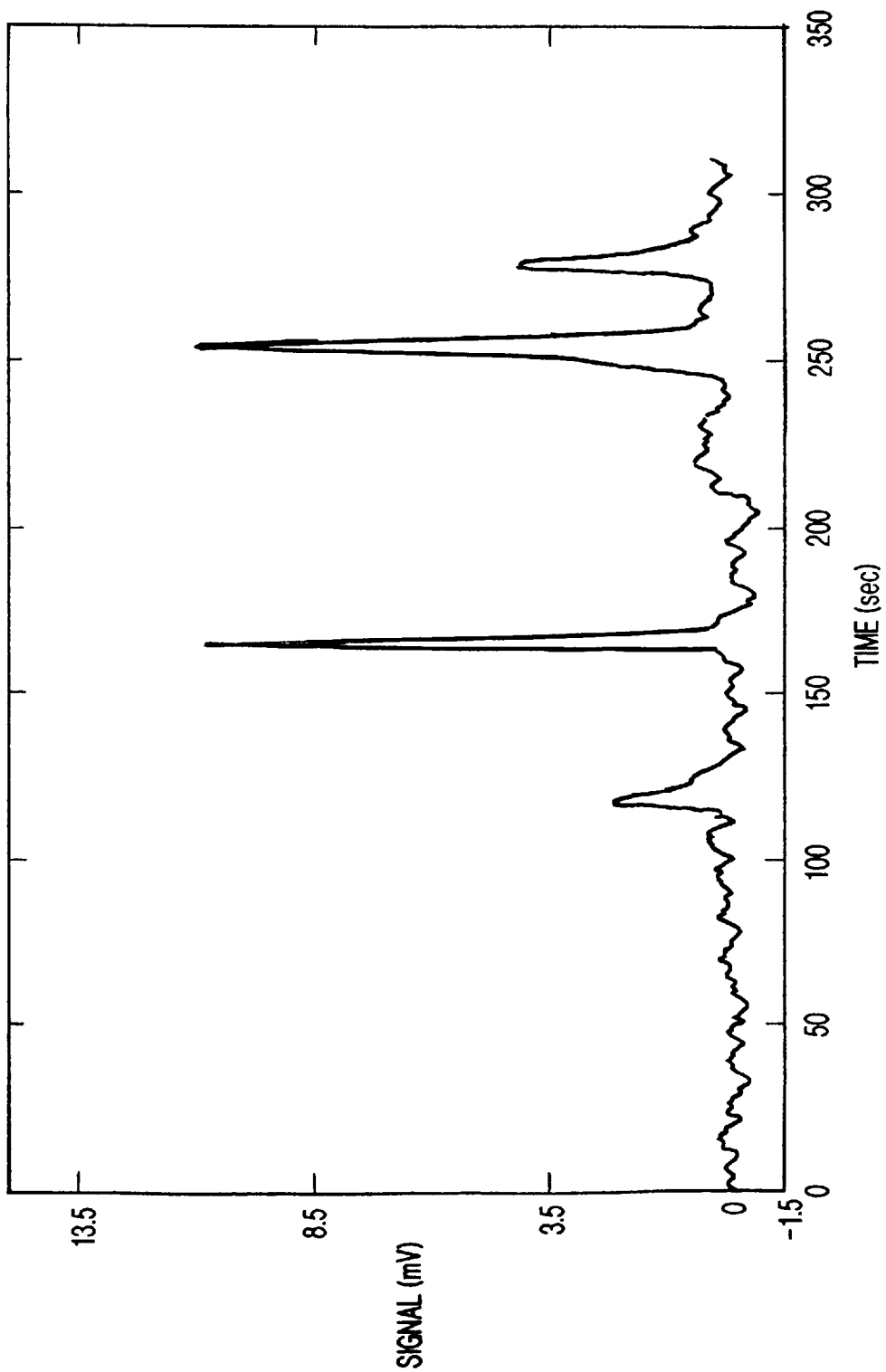
FIG. 4 is a representative output from an embodiment of the apparatus using helium as the reactant gas.

FIG. 4 shows a Varian 3700 signal output using helium as the inert gas and 1.5 ng TCE and 1.0 ng mixed xylenes as the analytes. FIG. 5 shows the output using argon as the reaction gas and gasoline vapor as the analyte.

Dielectric barrier discharge is a process that has unique applications to analytical chemistry. A DBD is a cell through which a gas can flow, of which at least two of the boundaries of the cell consist of a dielectric material such as ceramic, glass, or quartz. An alternating current ranging from 1 KV to 10's of KV (depending on the gas, temperature, gap, and pressure) is applied at frequencies ranging from 60 Hz to 10's of kHz to the dielectric material. The result of this process is the production of a streamer, wherein the ionization in the gas exceeds the electron attachment rate. When this occurs, charge is transferred from one dielectric barrier to the other. However, as charge is transferred from one barrier to the other, the source barrier becomes depleted in charge and the receiving barrier becomes enhanced in charge. This leads to a reduced field within that region of the DBD cell which extinguishes the streamer process. Because of the short, self-terminating nature of the streamers, only electrons can extract energy from the potential created across the cell barriers and the gas itself does not become hotter. Thus, DBD discharges yield electrons and metastable states in inert gases that can be utilized to excite a variety of analytes of interest.

Significant differences exist between generating the metastable reaction according to the present invention as compared to the prior art. First, unlike a microwave plasma, the DBD plasma will re-initiate even after being extinguished if a sufficient voltage is maintained across the electrode gap. Microwave plasmas require a "short" to re-initiate the plasma. Second, unlike pulsed sparks between metal electrodes, the DBD process is carried out in the presence of inert materials and so generates no electrode wear. Furthermore, unlike an arc process, the discharge in a DBD is not a thermal process. This is due to the self-terminating nature of the discharge within the dielectric materials as laid out in the discussion above. This means that the plasma can easily be maintained in a variety of gases without relying on the thermal conductivity of the reactant gas to prevent overheating of the electrodes. Thus the DBD can be operated in pure inert gases rather than just helium with other inert gases doped into the helium. Furthermore, because the DBD plasma is non-thermal, the system does not need to be operated in a pulsed mode to limit electrode wear. A continuous plasma can be utilized, without pulsing, to maintain a sufficiently high flux of reactive species. This results in an increased linear range for the detector since there are more active species available to react with the analyte of interest. Moreover, the DBD cell does not require high precision in the placement of the electrodes. This results in a plasma cell which is easy to construct and very inexpensive.

In the invention, the excited state gas is generated through the use of a dielectric barrier discharge, which excites a gas capable of transferring this energy to the analyte of interest. The dielectric barrier discharge is generated through the use of a chamber consisting of a dielectric material (e.g., quartz, glass, or ceramic) to which an AC voltage of significant intensity is applied to create the discharge. Hydrocarbons are degraded into a variety of products, one of which is CN. Secondary to this reaction, an additional reaction is initiated utilizing a ceramic bead heated sufficiently to produce a plasma at the boundary layer of the bead. This bead, known as a thermionic source, acts as a source of electrons to ionize hydrocarbon species containing nitrogen. These ionized species are then measured by a sensitive electrometer in a manner identical to that laid out above. In this mode, helium cannot be used as it will quench the active nitrogen species and extinguish the reaction. However, air can be introduced into this stream and still yield a sensitive method for detecting hydrocarbons.

There are a number of other advantageous aspects of the DBD plasma over those of the prior art. The plasma generated is capable of being made at both room temperature and at elevated temperatures. Since the plasma is generated in a separate cell which can be manufactured from inert materials, there are no limitations on temperature of the reactive zone. The system is capable of being operated at pressures above atmospheric. This is especially useful for applications such as gas chromatography, where the chromatographic column effluent is typically above atmospheric pressure, or in applications where compressed gases are being transported. It leads to further advantages over other discharge mechanisms in that it reduces the number of physical components required to support the detector such as pumping systems. Since the plasma is non-thermal, it does not require external cooling of any sort. The DBD based detector is also one which is devoid of radioactive sources and therefore, is not subject to strict licensing requirements as are required for traditional, radioactive material based detectors.

The use of helium as the reaction gas leads to the generation of excited state species for almost all compounds (all those that have ionization potentials less than 17.7 eV.) The use of lower purity helium is also possible with DBD since the DBD can sustain the plasma even in the presence of these interferences. However, the reproducibility of the detection will be more difficult since impurities in the helium stream can vary in concentration. Likewise, dopants, like those laid out by Wentworth et al., can be utilized to reduce the effective ionization potential of the reaction gas and provide a selective process for detection.

The use of pure argon in the DBD detector with an ionization potential maximum of 11.8 eV limits the number of species that can be detected to those with an ionization potential below this value. For example, any compound with an ionization potential below that of argon, (compounds such as hexane and methanol) can be detected using this scheme. However, compounds with an ionization potential above that of argon such as water, nitrogen, and hydrogen are not ionized and therefore not detected using this scheme. The ability to ionize pure argon as the reactant gas in the DBD, rather than helium doped with argon offers the advantage of providing significantly more reactive species to interact with the analytes of interest. As noted above, and as demonstrated by the work of Dodge et al., this has the net effect of increasing the linear range of the detector. In addition, the use of pure argon, rather than excited helium doped with argon means that the system can be utilized with nitrogen as a carrier stream since the nitrogen will largely be unaffected by the excited argon. (With helium doped with argon, the use of helium precludes the use of nitrogen since the nitrogen would be excited by the excited helium.) Moreover, the use of argon reactant gas will allow for trace of oxygen, water, and nitrogen to be present in the system without adversely affecting the performance of the analytical system. In this manner, the presence of trace impurities in argon, while not recommended, should not have too adverse an effect performance of the detector. Finally, argon is substantially cheaper than helium for this type of work which is advantageous to facilities which support large numbers of instruments.

The use of nitrogen as the reactant gas further limits those species which can be detected. For example, while direct ionization in nitrogen has not been measured utilizing a DBD, the DBD can generate active nitrogen (as noted in Dodge et al. and Capelle et al.) which can react with hydrocarbons to create CN compounds. These compounds, when passed over a thermionic source, can become ionized and, when a bias voltage is applied, attracted to an electrometer and measured.

In a further embodiment of the invention, the analyte is passed through a dielectric barrier discharge where it is reacted to produce a species more amenable to detection using the thermionic sources identified above. The advantage of operating in this mode, versus the traditional mode for thermionic sources (which utilizes a hydrogen/air mixture), is that little or no water is generated. Water generated by the combustion of the hydrogen/air mixture is the primary suspect in the deterioration of the thermionic source. This deterioration limits the useful life and sensitivity of current thermionic sources. This does not occur when utilizing a DBD with inert gases. Therefore, when using the DBD cell in conjunction with the thermionic bead source, the user can expect to obtain significantly longer lifetimes from the bead than would be possible with the flame bases version of this detector.

The DBD cell, unlike pulsed DC discharge cells, is able to continually generate active species within the source reign. This is the result of the distributed and continuous nature of the discharge which results in continuous replenishment of the active species. As a result, more of these species are available to react with the analytes of interest leading to an increased linear range.

The DBD cell can also be used with an inert gas doped with a different gas, typically nitrogen, to substantially increase the breakdown voltage in the DBD. This is advantageous in the generation of higher power states in the DBD configuration in order to apply used as a means of detection.

In a further embodiment of the invention, in order to minimize the generation of energy states which are too high in the presence of nitrogen, a dielectric packing material is placed between the electrodes.

Utilizing breakdown voltages ranging from a very efficent plasma may be employed. The source is capable of exciting a wide variety of gases under these conditions including helium, nitrogen, and argon. These gases can then be mixed with other components which result in a transfer of energy from the reactant gas to the analyte. The analyte can then be measured using an electrometer.

The advantages of the invention include the following. First, the generation of active nitrogen is done on a very low flow which is advantageous to chromatograghy. Second, the use of active nitrogen for the sensitive and selective detection of hydrocarbons allows detection specific to hydrocarbons. Such a detector may be used in the petroleum industry, for example, for the measurement of fuel stocks. An added advantage of the detector is the added safety of not using a hydrogen based flame as is found in the FID.

The invention is easily configured to use very low flows (on the order of 10–50 mL/min) of the reaction gas. This is advantageous because it minimizes the power requirements necessary to drive the plasma leading to a safer and more cost effective device. It also minimizes the usage of gases which are typically expensive to obtain at higher purity.

Additional advantages of the invention include the ability to operate over numerous excitation sources. Since the DBD plasma is non-thermal, the discharge is capable of being operated with a variety of inert gases such as nitrogen, argon, and helium. This provides selectivity in the compounds that can be detected.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents, The entire disclosures of all references, applications, patents, and publications cited above are hereby incorporated by reference.

What is claimed is:

1. A method for detection of trace constituents, the method comprising the steps of:
   a) forming a dielectric barrier discharge by applying an alternating current voltage across a dielectric barrier material;
   b) elevating the inert gas to an excited state via the dielectric barrier discharge;
   c) mixing the excited state inert gas with trace analytes; and
   d) measuring with an electrometer matter selected from the group consisting of the analytes and their byproducts.

2. The method of claim 1 wherein the elevating step comprises maintaining the inert gas at a pressure above atmospheric pressure.

3. The method of claim 1 wherein the elevating step comprising maintaining the inert gas at a temperature approximately at or above room temperature.

4. The method of claim 1 additionally comprising the step of providing one or more reaction gases to pass through the dielectric barrier discharge.

5. The method of claim 4 wherein the providing step comprises providing one or more reaction gases comprising one or more dopants.

6. An analyte detection apparatus comprising:
   an inert gas source;
   a reaction cell;
   a dielectric barrier discharge cell connected to said inert gas source and said reaction cell wherein said dielectric barrier discharge cell excites the inert gas which is commingled with the analyte of interest to produce charged species; and electrometer means for measuring the species.

7. The apparatus of claim 6 wherein said dielectric barrier discharge cell comprises a material selected from the group consisting of ceramic, quartz, and glass.

8. The apparatus of claim 6 wherein said dielectric barrier discharge cell comprises an alternating current voltage source operating at a frequency between approximately 60 Hz and 100 kHz and at a voltage between approximately 1 kV and 100 kV.

9. The apparatus of claim 6 wherein said inert gas source comprises an inert gas selected from the group consisting of argon, helium, nitrogen, xenon, krypton, neon, and mixtures thereof.

10. The apparatus of claim 6 additionally comprising means for applying a bias voltage to a device selected from the group consisting of the reaction chamber, a collector, and combinations thereof.

11. The apparatus of claim 10 wherein said means for applying a bias voltage comprises means for continuously applying a bias voltage.

12. The apparatus of claim 10 wherein said means for applying a bias voltage comprises means for pulsing the bias voltage.

13. The apparatus of claim 6 wherein said dielectric barrier discharge cell comprises an electrode covered with a dielectric material.

* * * * *